(12) United States Patent
Bendahan (10) Patent No.: US 8,483,356 B2
(45) Date of Patent: Jul. 9, 2013

(54) MOBILE AIRCRAFT INSPECTION SYSTEM

(75) Inventor: Joseph Bendahan, San Jose, CA (US)

(73) Assignee: Rapiscan Systems, Inc., Torrance, CA (US)

( * ) Notice: Subject to any disclaimer, the term of this patent is extended or adjusted under 35 U.S.C. 154(b) by 333 days.

(21) Appl. No.: 12/916,371

(22) Filed: Oct. 29, 2010

(65) Prior Publication Data

US 2011/0103548 A1    May 5, 2011

Related U.S. Application Data

(60) Provisional application No. 61/256,104, filed on Oct. 29, 2009.

(51) Int. Cl.
| G01N 23/04 | (2006.01) |
| G01N 23/02 | (2006.01) |
| H05G 1/02  | (2006.01) |

(52) U.S. Cl.
USPC ............................... 378/57; 378/53; 378/197

(58) Field of Classification Search
USPC .................. 378/51, 54–57, 62, 76, 189, 193, 378/197, 198
See application file for complete search history.

(56) References Cited

U.S. PATENT DOCUMENTS

| | | | |
|---|---|---|---|
| 5,014,293 A | 7/1991 | Boyd et al. | |
| 5,363,940 A | 11/1994 | Fahrion | |
| 5,692,029 A | 11/1997 | Husseiny et al. | |
| 6,220,099 B1 | 4/2001 | Marti et al. | |
| 6,292,533 B1 | 9/2001 | Swift et al. | |
| 6,614,872 B2 | 9/2003 | Bueno et al. | |
| 6,763,635 B1 * | 7/2004 | Lowman ........................ 52/114 |
| 6,888,640 B2 | 5/2005 | Spina et al. | |
| 6,950,495 B2 | 9/2005 | Nelson et al. | |
| 6,950,719 B2 | 9/2005 | Landers et al. | |
| 7,024,272 B2 | 4/2006 | Thomas et al. | |
| 7,069,192 B1 | 6/2006 | Freitag | |
| 7,086,028 B1 | 8/2006 | Davis et al. | |
| 7,099,434 B2 | 8/2006 | Adams et al. | |
| 7,103,434 B2 | 9/2006 | Chernyak et al. | |
| RE39,396 E * | 11/2006 | Swift et al. ........................ 378/57 |
| 7,151,447 B1 | 12/2006 | Willms et al. | |
| 7,203,276 B2 | 4/2007 | Arsenault et al. | |
| 7,218,704 B1 | 5/2007 | Adams et al. | |
| 7,224,772 B2 | 5/2007 | Jacobs et al. | |
| 7,280,990 B2 | 10/2007 | Turner et al. | |
| 7,305,063 B2 | 12/2007 | Heuscher | |
| 7,508,910 B2 | 3/2009 | Safai et al. | |
| 7,623,626 B2 | 11/2009 | Safai et al. | |
| 2001/0016803 A1 | 8/2001 | Sartiono et al. | |
| 2003/0043964 A1 * | 3/2003 | Sorenson ........................ 378/58 |
| 2004/0264626 A1 | 12/2004 | Besson | |
| 2006/0114477 A1 | 6/2006 | Cox et al. | |
| 2007/0189454 A1 | 8/2007 | Georgeson et al. | |
| 2007/0269006 A1 | 11/2007 | Safai et al. | |
| 2008/0205594 A1 | 8/2008 | Bjorkholm | |
| 2009/0168964 A1 | 7/2009 | Safai et al. | |
| 2009/0238336 A1 | 9/2009 | Akery | |
| 2009/0245462 A1 | 10/2009 | Agrawal et al. | |
| 2010/0034355 A1 | 2/2010 | Langeveld et al. | |
| 2010/0295689 A1 | 11/2010 | Armistead et al. | |

OTHER PUBLICATIONS

PCT/US10/054859 Search Report, Mar. 21, 2011.

* cited by examiner

*Primary Examiner* — Anastasia Midkiff
(74) *Attorney, Agent, or Firm* — Novel IP (57) ABSTRACT

A system for scanning aircraft for concealed threats is provided. The system comprises a vehicle and a manipulator arm attached with a scanning head that can be maneuvered in multiple directions to completely scan an aircraft from the outside. The system uses transmission based X-ray detection, backscatter based X-ray detection or a combination thereof, in various embodiments. The system also includes gamma-ray and neutron detectors, for detection of nuclear and radio-active materials.

11 Claims, 10 Drawing Sheets

MOBILE AIRCRAFT INSPECTION SYSTEM

CROSS-REFERENCE TO RELATED APPLICATIONS

The present invention relies on U.S. Provisional Patent Application No. 61/256,104, entitled "Mobile Aircraft Inspection System" and filed on Oct. 29, 2009, for priority and is herein incorporated by reference in its entirety.

FIELD OF THE INVENTION

The present invention generally relates to the field of radiant energy imaging systems for detecting concealed objects, and more specifically to an X-ray inspection system for inspecting aircraft for threat items and other contraband.

BACKGROUND OF THE INVENTION

In current times, with increasing threats of violence, the inspection of vehicles in addition to luggage and cargo at transit points has become almost universally mandatory. In addition to passenger and cargo vehicles, contraband such as explosives, weapons, narcotics, dangerous chemicals, and nuclear and radioactive materials can also be concealed in various parts of general aircraft for illegal transportation. Detection of such contraband and presence of other threat items in an aircraft requires detailed inspection of the aircraft in its entirety.

Amongst detection systems that provide for efficient non-invasive inspection, X-ray imaging systems are the most commonly used. Transmission based X-ray imaging systems are traditionally used to inspect trucks and cargo containers for contraband. Inspection of a complete aircraft however, can be challenging with a transmission-based geometry wherein typically, the source is located on one side of the aircraft and detectors are located on the other side of the aircraft. This geometry has many challenges, and in particular, when scanning around the landing gear and engines as there is difficulty placing detectors and thus, in producing radiographic images.

In backscatter based inspection systems, X-rays are used for irradiating a vehicle or object being inspected, and rays that are scattered back by the object are collected by one or more detector arrays. The resultant data is appropriately processed to provide images which help identify the presence of contraband. In transmission systems, the radiation source is placed on one side of the object while the detectors are placed on the other side. The radiation source and detectors are maintained in fixed alignment relative to each other.

Since aircraft are typically made of lighter materials, a backscatter-based detection system would provide adequate penetration in most cases and thus would only require equipment to be placed on one side of the aircraft. However, backscatter technology may not be suitable when all areas of the aircraft have to be penetrated with a high detection probability, such as is the case with nuclear materials detection. Areas of high attenuation as measured by the backscattered radiation include fuel tanks, transformers, counterweights, among other aircraft components. In addition, backscatter technology cannot effectively discriminate between typical metals and special nuclear materials.

Aircraft inspection calls for unique requirements such as the capability of inspecting large aircraft from more than one side. In addition, varying aircraft sizes would require the inspection head to scan at different heights, and several sections of the aircraft, such as the wings and tails, would require different head and detector scanning configurations. Conventional X-ray backscatter and transmission systems, however, do not have adequate scanning robustness, ability to work in various orientations, scanning range, or field of view for aircraft inspection applications.

Therefore, what is needed is a rapid and accurate inspection system for determining the presence of concealed illegal materials, both nuclear and non-nuclear, in general aviation aircraft.

What is also needed is a system that is easily transportable, mobile, and non-intrusive, that is capable of operating even in rugged outdoor conditions such as airport environments.

SUMMARY OF THE INVENTION

In one embodiment, the present invention is a mobile, non-intrusive inspection system capable of inspecting aircraft in its entirety for nuclear and other contraband materials. In one embodiment, the inspection system of the present invention is capable of detecting weapons, drugs, or other contraband hidden even in those areas of the aircraft, which are difficult to scan, such as the voids of the wings, fuselage, engine nacelles, empennage, and stabilizer areas.

The inspection system of the present invention is not only rapid and non-intrusive, but also safe for all personnel in the immediate area of the aircraft, including the system operator, ground personnel and personnel on the aircraft. The system of the present invention is, in one embodiment, designed to be mobile, such that it can be delivered to any airfield and operate independently from other equipment and machines on the airfield.

In one embodiment, the present invention is a system for scanning an aircraft from the outside for the detection of concealed threats, comprising: a scanning head comprising an X-ray source for generating an X-ray beam toward the aircraft; a manipulator arm for maneuvering the scanning head relative to the aircraft, wherein said manipulator arm has a first end and a second end, wherein the first end is movably connected to a vehicle for transporting the system and wherein the second end is movably connected to the scanning head; a movable detector unit comprising a first set of detectors, said detector unit being aligned with said scanning head such that the first set of detectors receive the X-rays transmitted through the aircraft; a computer system for controlling the motion of the system, wherein said computer system further comprises a memory.

In one embodiment, the scanning head further comprises at least one proximity sensor.

In another embodiment, the scanning head further comprises a second set of detectors for receiving X-rays that are backscattered from the aircraft.

In one embodiment, the positions of the X-ray source and the first set of detectors are synchronized remotely. In one embodiment, the X-ray source and the first set of detectors are positioned along opposite sides of the aircraft.

In one embodiment, the detector unit is L-shaped to capture X-rays transmitted through the aircraft.

In one embodiment, the manipulator arm has a plurality of degrees of freedom for positioning the scanning head, wherein said plurality of degrees of freedom includes at least one of up, down, left, right, in, out, and rotation.

In one embodiment, the computer system for controlling the motion of the system further includes a database of at least one plane contour stored in the memory for controlling said motion based on said plane contour.

In one embodiment, images are displayed on a monitor for local or remote viewing by an operator. In one embodiment, images are compared with images collected from planes of the same model to determine anomalies.

In one embodiment, the detected threats include organic materials, inorganic materials and nuclear materials. In one embodiment, the system further includes gamma-ray detectors and neutron detectors for detection of nuclear and radioactive materials in passive mode and for detection of nuclear materials following radiation induced by photofission.

In one embodiment, present invention is a system for externally scanning an aircraft, having a body and an underside, to detect concealed threats, the system comprising: a mobile gantry defined by two vertical beams connected by a horizontal beam, wherein the horizontal beam comprises a top side of said gantry, and wherein said gantry is capable of being moved along the length of the aircraft being scanned; an X-ray source connected to the top side of said gantry, said source capable of being moved horizontally along the top side; and a movable detector unit comprising a first set of detectors, said detector unit being aligned with said X-ray source and being positioned along the underside of the aircraft, such that the first set of detectors receive X-rays transmitted through the aircraft from said X-ray source.

In one embodiment, the positions of the X-ray source and the first set of detectors are synchronized remotely.

In one embodiment, the scanning motion comprises moving the mobile gantry along the length of the aircraft and moving the X-ray source along the width of the aircraft.

In one embodiment, the system comprises a second set of detectors disposed on the top side of said gantry for receiving the X-rays scattered back from the aircraft.

In one embodiment, the X-ray source is capable of being tilted in at least four directions.

In one embodiment, detected threats include organic materials, inorganic materials and nuclear materials.

In one embodiment, the present invention is a system for externally scanning an aircraft, having a body and an underside, to detect concealed threats, the system comprising: a mobile gantry defined by two vertical beams connected by a horizontal beam, wherein the horizontal beam comprises a top side of said gantry, and wherein said gantry is adapted to move over at least one section of the aircraft being scanned; a transverse beam, having a first end and a second end, coupled to the top side of said gantry, adapted to be moved horizontally along the said top side, wherein an X-ray source is connected to the first end of said transverse beam and a counterweight is connected to the second end of said transverse beam to balance said X-ray source; and a movable detector unit comprising a first set of detectors, said detector unit being aligned to the X-ray source, such that the first set of detectors receive X-rays transmitted through the aircraft from said X-ray source.

In one embodiment, the system of the present invention further comprises a second set of detectors disposed along with the X-ray source for receiving the X-rays scattered back from the aircraft.

In one embodiment, the X-ray source is capable of being tilted in four directions.

In one embodiment, the positions of said X-ray source and said first set of detectors are synchronized remotely.

In one embodiment, the detected threats include organic materials, inorganic materials and nuclear materials.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION OF THE INVENTION

The present invention is directed towards a mobile, non-intrusive inspection system capable of inspecting aircraft in its entirety, and in particular a complete general aviation aircraft, for nuclear and other contraband materials. In one embodiment, the system of the present invention is capable of detecting weapons, drugs, or other contraband hidden even in those areas of the aircraft, which are difficult to scan, such as the voids of the wings, fuselage, engine nacelles, empennage, and stabilizer areas. The inspection system of the present invention is not only rapid and non-intrusive, but also safe for all personnel in the immediate area of the aircraft, including the system operator, ground personnel and personnel on the aircraft. The system of the present invention is, in one embodiment, designed to be mobile, such that it can be delivered to any airfield and operate independently from other equipment and machines on the airfield.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In one embodiment, the basic inspection mode is to use a single-energy and the lowest-energy linac that would allow penetration of the aircraft and detection of the nuclear materials of interest. These images are then analyzed to determine the presence of high-density and high-atomic objects and to distinguish these from benign materials. To maintain a low dose to the surrounding environment, the x-ray source is designed such that it allows for reduction of the beam current for areas with low attenuation and increased beam current to allow penetration of highly attenuating objects.

U.S. patent application Ser. No. 12/780,910, entitled "Systems and Methods for Automated, Rapid Detection of High Atomic Number Materials", and filed on May 16, 2010 is herein incorporated by reference in its entirety. In addition, U.S. patent application No. 12/484,172, entitled "Systems and Methods for Using an Intensity-Modulated X-ray Source", and filed on Jun. 12, 2009, is herein incorporated by reference in its entirety.

The system can also employ dual-energy scanning, in interlaced and non-interlaced modes, to enhance the detection of nuclear materials. The system can also employ energy sensitive detectors with the single or dual-energy scanning.

In one embodiment, the present invention employs X-ray backscatter imaging although one of ordinary skill in the art would appreciate that aircraft screening may be performed using any available radiation imaging technique. For the purpose of aircraft inspection based on backscatter technology, in one embodiment the X-ray energy delivered by the source is optimized to be in the range of 150 kV to 450 kV. This range allows adequate penetration of the aluminum shell and other parts of the aircraft. For better quality of imaging and to allow for shorter inspection times, the beam current is also optimized to appropriate levels, especially since the dose of radiation delivered to the aircraft is less of a concern. In one embodiment, the beam scanning mechanism further comprises a beam chopper, and is designed to include shielding material as well. In one embodiment, the angle of the X-ray beam with respect to the normal to the front of the detector head is kept preferentially at about 10 degrees. This angle avoids going through the full length of objects that are commonly vertical, and provides some depth information to the screener. It should be appreciated that other ranges of energy levels may be used and other forms of radiation or energy can be used, including gamma, millimeter wave, radar or other energy sources.

Further, a second embodiment of the present invention is described with reference to X-ray transmission imaging. For the purpose of aircraft inspection based on transmission technology, the X-ray energy is optimized in the range of 200 kV to 1 MV, when detection of nuclear materials is not required, depending on the size of the aircraft. The optimized energy range increases from 1 MV to 9 MV when nuclear material detection is required. The source could generate a single-energy distribution or multiple-energy distributions.

Still further, in a third embodiment, the present invention advantageously employs both backscatter and transmission imaging. Thus, any imaging system that has the potential for displaying object detail may be employed in the system and methods of the present invention.

Figure 1:
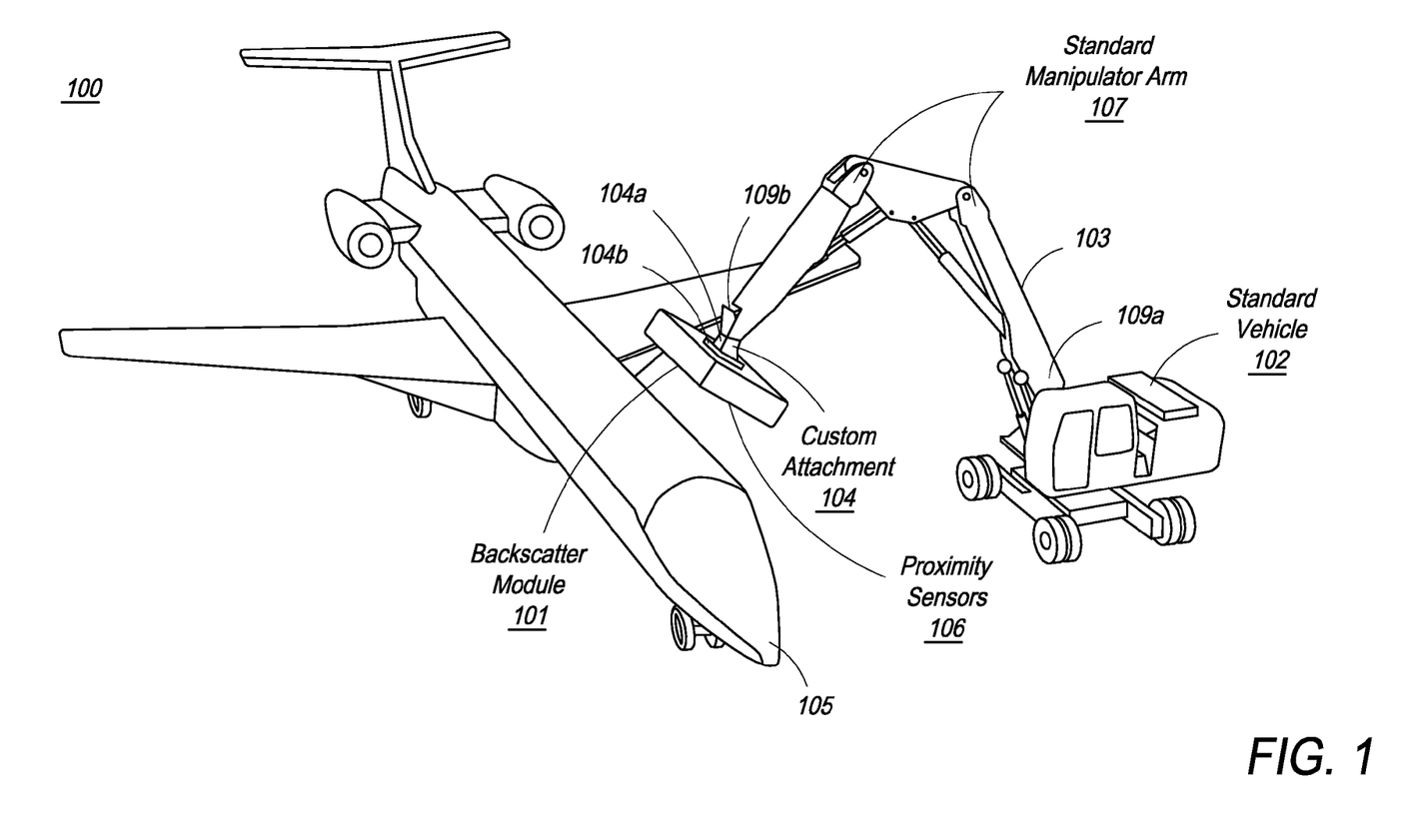
FIG. 1 illustrates a functional design of the backscatter-based aircraft inspection system of present invention.

FIG. 1 illustrates the overall system design of one embodiment of the present invention. Referring to FIG. 1, aircraft inspection system 100, in one embodiment, comprises inspection head 101, vehicle or transport cart 102, and manipulator arm 103. In one embodiment, inspection head 101 comprises a backscatter inspection module, further comprising an X-ray source, a beam scanning mechanism and X-ray detectors. The backscatter inspection module is described in greater detail below with respect to FIG. 4. In one embodiment, vehicle or transport cart 102 is any standard vehicle suitable for movement about an aircraft 105.

In one embodiment, vehicle 102 is movably connected to first, proximal end 109a of manipulator arm 103 and inspection head 101 is movably connected to second, distal end 109b of manipulator arm 103 via a customized attachment 104. Manipulator arm 103 is described in greater detail below. In one embodiment, customized attachment 104 is designed for use with the system of the present invention. In another embodiment, customized attachment 104 may be available as an off-shelf component, as long as it achieves the objectives of the present invention, as described below.

In one embodiment, the inspection head 101 is mounted on manipulator arm 103 in such a manner that it allows for scanning of a variety of aircraft sizes, shapes and configurations. The manipulator arm 103 is also capable of rotating and moving the inspection head 101 in all directions. In one embodiment, customized attachment 104 is movably attached to manipulator arm 103 at a first joint 104a and movably attached to inspection head 101 at a second joint 104b. Thus customized attachment 104 allows for the inspection head 101 to be moved and rotated about first joint 104a and second joint 104b. In one embodiment, first joint 104a and/or second joint 104b is a ball and socket type joint that allows for at least one movement, such as but not limited to tilt, swivel and/or rotation at the joint, and in one embodiment, full motion. The ability to move and rotate the source at both the first attachment joint 104a and at the second attachment joint 104b allow for the system to follow the contour of the aircraft and thus, adjust to its shape using several degrees of movement freedom.

Figure 3A:
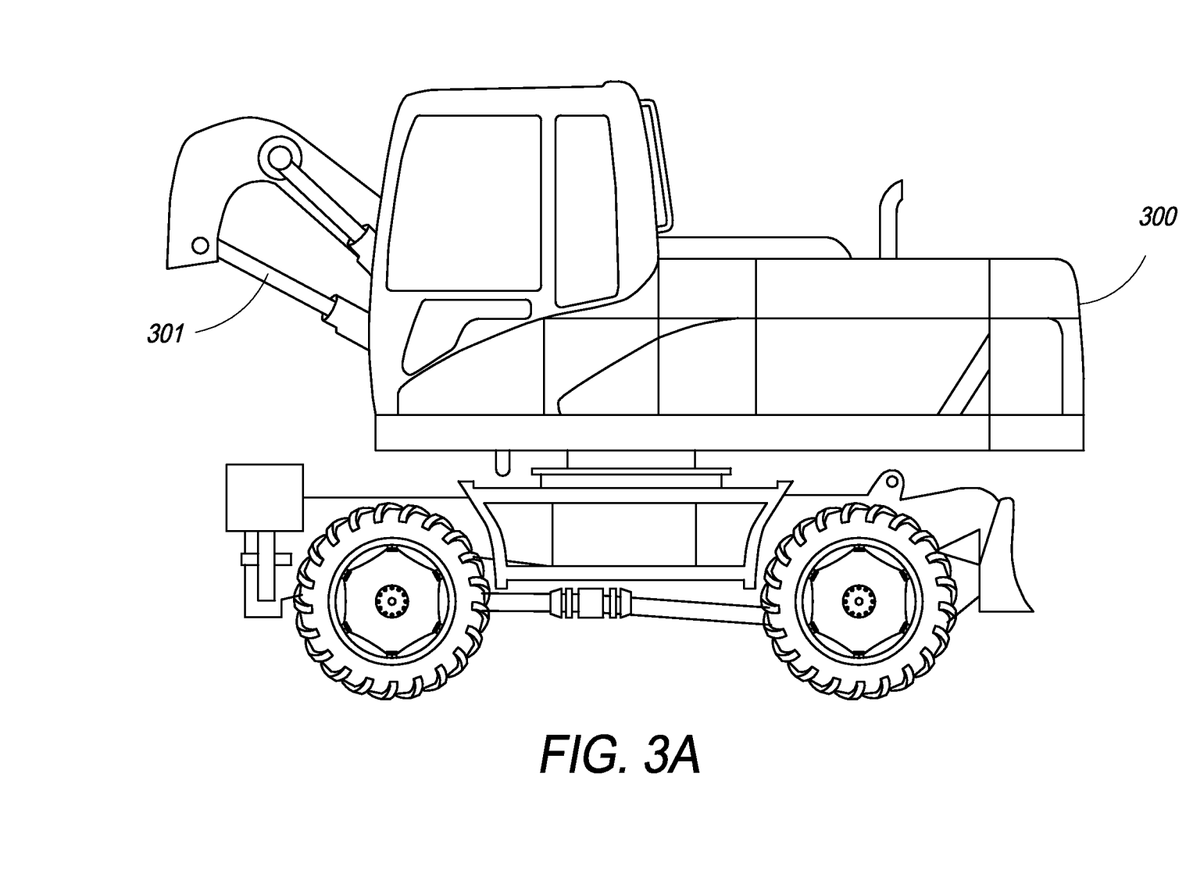
FIG. 3A illustrates an exemplary vehicle that can be used with the mobile aircraft inspection system of the present invention.
Figure 3B:
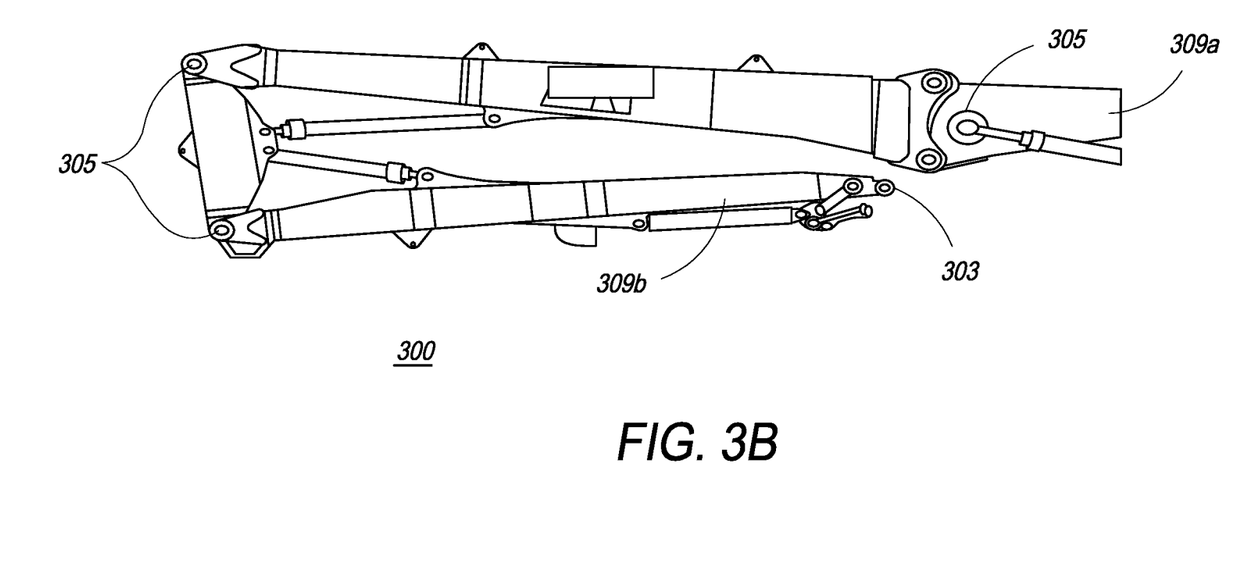
FIG. 3B illustrates an exemplary manipulator arm used for mounting the inspection head or radiation source of the system of present invention.

In addition, manipulator arm 103 has multiple articulation or pivot joints 107 that allow for complex motions, shown in greater detail and described with respect to FIG. 3B.

In one embodiment, in order to avoid damage to the aircraft 105 being inspected, the inspection head 101 includes at least one proximity sensor 106. In one embodiment, the sensors are redundant, so if one fails to operate, another sensor will still alert when the system is too close to the aircraft. The at least one proximity sensor 106 is configured to avoid collision and keep the inspection head 101 at a safe distance from the aircraft 105. Therefore, once the at least one proximity sensor 106 is triggered, the inspection system 100 will cease operation. When inspection system 100 ceases operation, the scanning head is retracted and the system cannot be operated until the sensor alarm is cleared.

In one embodiment, the at least one proximity sensor 106 is connected and controlled via hardware.

In one embodiment, manipulator arm 103 includes at least one proximity sensor. In one embodiment, vehicle 102 also includes at least one proximity sensor.

Figure 2:
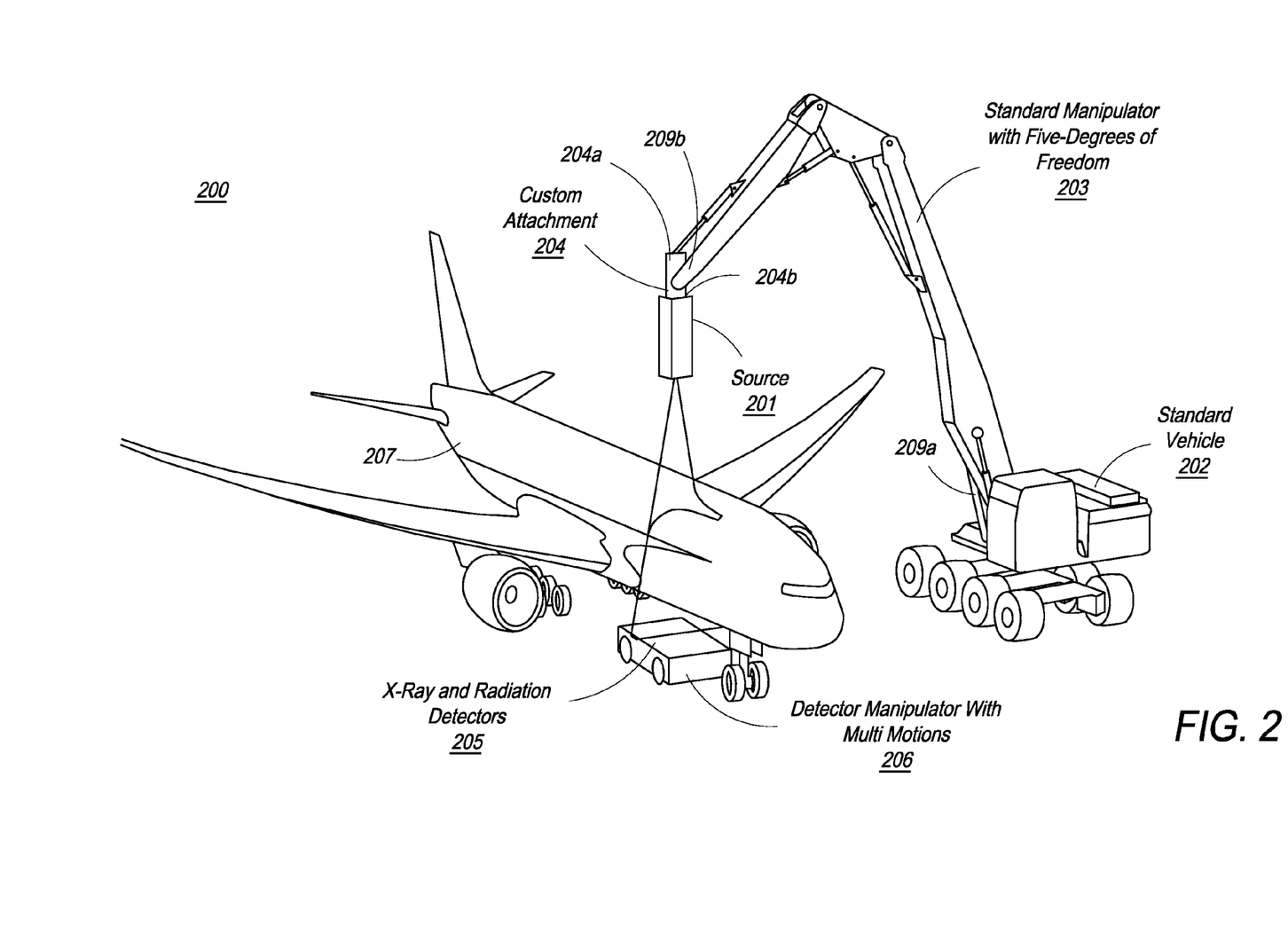
FIG. 2 illustrates a functional design of the transmission-based aircraft inspection system of present invention.

FIG. 2 illustrates the overall system design of another embodiment of the aircraft scanning system of the present invention. Referring now to FIG. 2, aircraft inspection system 200, in one embodiment, comprises X-ray source 201, vehicle or transport 202, a source manipulator 203, an X-ray detector array 205 and a detector manipulator 206, which houses detector array 205. In one embodiment, detector manipulator 206 comprises a multi-directional cart that has several degrees of freedom.

In one embodiment, vehicle 202 is movably connected to first, proximal end 209a of manipulator arm 203 and X-ray source 201 is movably connected to second, distal end 209b of manipulator arm 203 via a customized attachment 204. Manipulator arm 203 is described in greater detail below.

"In one embodiment, X-ray source 201 is mounted on manipulator arm 203 in such a manner that it allows for scanning of a variety of aircraft sizes, shapes and configurations. The manipulator arm 203 is also capable of rotating and moving source 201 in all directions. In one embodiment, customized attachment 204 is movably attached to manipulator arm 203 at a first joint 204a and movably attached to X-ray source 201 at a second joint 204b. Thus customized attachment 204 allows for the X-ray source 201 to be moved and rotated about first joint 204a and second joint 204b. The ability to move and rotate the source at both the first attachment joint 204a and at the second attachment joint 204b allow for the system to follow the contour of the aircraft 207 and thus, adjust to its shape using several degrees of movement freedom."

In one embodiment, the radiation source and transmission detectors operate via remote synchronization. Thus, the system is able to determine the position of the source and the source's aiming point. In one embodiment, remote synchronization is achieved by collecting position information, subsequently gathered into a beacon, or set of beacons, using triangulation methods, which, in turn, use radio wave timing and logic signaling for best accuracy. The radio waves are preferably used over the line of sight, since there are generally obstacles near and around the detector system. In one embodiment, the beacons are located in a known position from the aircraft under inspection. The detector array 205 (via its computing system), and thus, the detector manipulator 206 housing the detector array 205 gathers information from the source or manipulator arm connected to the source to generate a source position, calculates the best position and angle of the detectors based upon the source position, and subsequently moves in relation to the source position.

In another embodiment, the synchronization is performed by the detector manipulator 206 following the source of radiation based on the feedback from the signals measured by the detector array 205. In this embodiment, the detector manipulator 206 moves in order to maximize the measured signals.

In one embodiment, remote synchronization can be achieved by placing at least one position sensor and transmitter in the scanning head and/or detector and communicating such position information to a controller, which may be located in the vehicle or a separate control station. In one embodiment, a GPS sensor and transmitter are employed. In one embodiment, the GPS sensor and transmitter communicate both scanning head and detector position information wirelessly to the controller. In one embodiment, the current detector position is determined using the GPS sensor and wirelessly communicated to the controller. In one embodiment, the current scanning head position is determined using the GPS sensor and is wirelessly communicated to the controller. The controller then wirelessly communicates the required detector position based upon the position of the scanning head and detector movement instructions to a controller on the detector unit. A motor that operates based upon directions from the controller unit in the detector system moves the detector to the requisite position. The process is repeated until all scan angles are taken.

In another embodiment, inertial sensors are employed at both the source and detectors, with position information wirelessly transmitted such that source and detector positions can be adjusted.

To select appropriate design specifications for the vehicle and the manipulator arm, the critical areas of focus are: a) the distance from the source/detector to the aircraft, b) the controlled motion of the source/detector, and c) collision avoidance for both the vehicle and the manipulator with the aircraft. In one embodiment, an optimal distance from the source/detector arrangement to the aircraft rages from ½ meter up to two meters. In one embodiment, the distance is chosen to provide optimal image resolution, inspection coverage and signal strength. The weight of the source/detector in conjunction with the maximum height and maximum reach that the manipulator arm must obtain further determines the dimensions of the vehicle platform. It should be understood by those of ordinary skill in the art that the weight of the source is largely dependent on source type, and that source type is chosen based on the object under inspection and scanning requirements. Scanning sequence, motion speed, and tolerances for position and vibration also direct the specifications for the manipulator arm and/or any special attachments or tooling. As mentioned earlier, in order to minimize development time and costs in one embodiment, any suitable off-the-shelf vehicle and/or manipulator arm may be employed and modified as per the design requirements of the present invention. In one embodiment, the height and reach of the manipulator arm and weight and/or dimensions of the inspection head are a function of the size of the airplane or large cargo containing entity being scanned.

FIG. 3A illustrates an exemplary vehicle 300 that is connected to a backscatter or transmission module (not shown), via manipulator arm 301, for the aircraft inspection system of the present invention. In one embodiment, for example, the vehicle 300 may be a wheeled excavator or a similar vehicle.

FIG. 3B illustrates an exemplary manipulator arm 300 that is used for mounting a backscatter or transmission module (not shown) for the aircraft inspection system of the present invention. In one embodiment, the manipulator arm 300 comprises a multi-purpose hydraulic boom. The boom design allows for the flexibility of attaching the vehicle (not shown) to a first, proximal end 309a while attaching standard or custom tools at its second, distal end 309b. Second, distal end 309b, in one embodiment, is modified to allow for attachment of a backscatter or transmission inspection module at joint 303.

In one embodiment, manipulator arm 300 is operated using computer-controlled motion and has at least five degrees of freedom for positioning in all directions, including up-down, left-right, in/out and rotation. In one embodiment, the system further comprises a controller unit, which can be remote from the system or located within the vehicle, for communicating motion instructions to controllers located in the scanning head or gantry unit which, in turn, directs motors to move the scanning head and/or gantry unit in the requisite direction. One method of controlling motion of the vehicle and the manipulator arm using a computer involves referring to a database of airplane models, stored in a memory on the computing system. Each entry in the database corresponds to a plane contour. This database enables the motion-control program to generate a scan plan, which is used to control the motion of the arm and the head to scan the airplane according to the plan. Further, for some planes, it may not be possible to scan the entire plane from one vehicle position. Therefore, the motion control program analyzes the various positions required and the system scans the plane accordingly.

In one embodiment, the arm is capable of full 360 degree rotation. The manipulator 300 is linearly extensible and contractible, and the extension and contraction can be achieved with a complex motion of the various parts of the manipulator arm. The system scans the aircraft by moving the arm at a nearly constant distance from the surface of the aircraft.

The manipulator arm 300 is also equipped with the capability of source rotation at the joint 303, as described above. The ability to rotate and move the source through several degrees of freedom at attachment joint 303, allow for the system to follow the contour of the aircraft and thus, adjust to its shape. The manipulator arm of the present invention has multiple articulation or pivot points 305 that allow for complex motions, including but not limited to extension and contraction.

Figure 4:
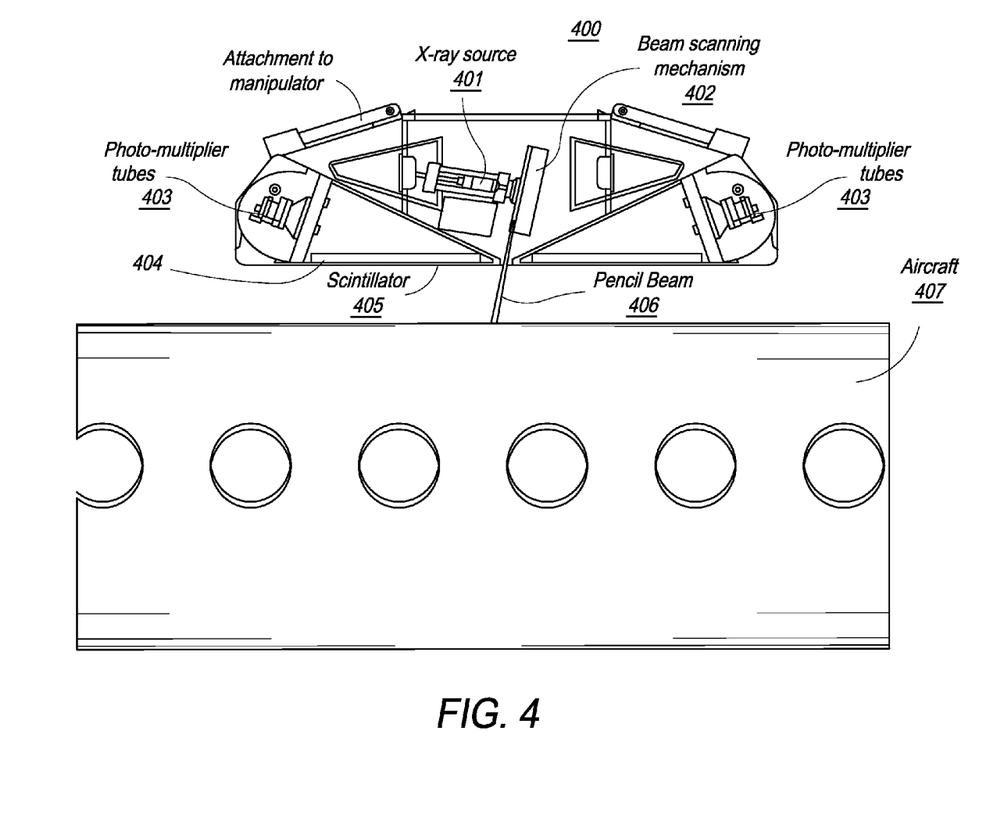
FIG. 4 is a cross-sectional view of a backscatter head of the present invention comprising a backscatter module.

FIG. 4 is a cross-sectional view of a backscatter inspection head of the present invention used in one embodiment of the imaging system of the present invention, as shown in FIG. 1, comprising a backscatter module. In one embodiment, backscatter module 400 comprises X-ray source 401, a beam scanning mechanism 402, and X-ray detectors 403. A front panel 404 of backscatter module 400 employs a scintillator material 405, which detects the backscattered X-rays, after a pencil beam 406 of X-rays is scanned over the surface of the aircraft 407 being inspected.

Figures 5A, 5B, 5C:
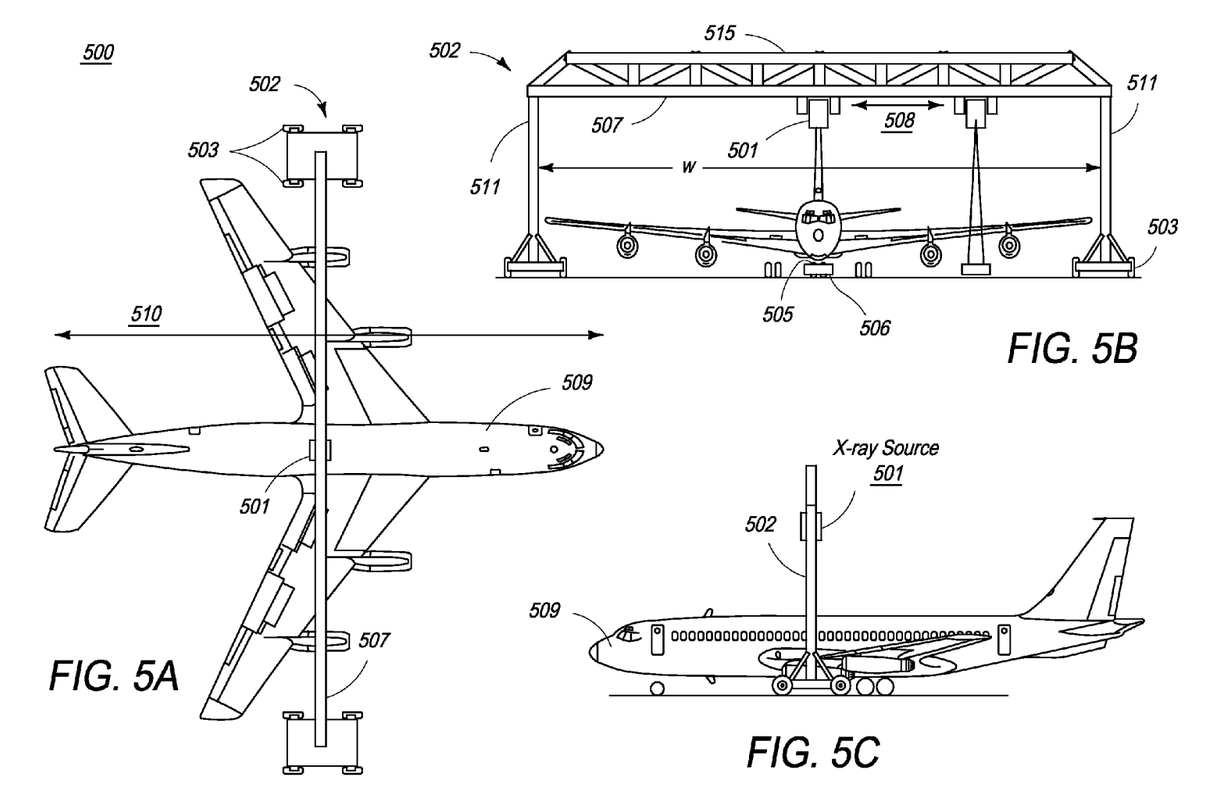
FIG. 5A is a top plan view of a single-scan transmission-based aircraft inspection system where the source is mounted on a movable crane in accordance with another embodiment of the present invention.
FIG. 5B is a front elevation view of the transmission-based aircraft inspection system, shown in FIG. 5A, where the source is mounted on a movable crane in accordance with another embodiment of the present invention.
FIG. 5C is a side elevation view of the transmission-based aircraft inspection system, shown in FIGS. 5A and 5B, where the source is mounted on a movable crane in accordance with another embodiment of the present invention.

FIGS. 5A through 5C shows another embodiment of the aircraft inspection system 500 of the present invention, in which the entire plane can be scanned in one single motion. In one embodiment, aircraft inspection system 500 is employed with relatively small planes for which the system can be designed such that it does not require a large footprint or a large, dedicated floor plan. In one embodiment, the inspection system 500 is an X-ray transmission-based system.

Referring to FIGS. 5A through 5C simultaneously, system 500 comprises a mobile overhead crane 502, whereby crane 502 comprises two substantially parallel vertical beams 511, which forms the two sides of crane 502, connected by a horizontal beam 507, which forms the top side of crane 502 thus forming a three-sided inspection gantry 515.

In one embodiment, crane 502 is movable along the length of the aircraft as shown by arrow 510, using wheels 503 connected to vertical beams 511. The radiation source 501 is mounted on the horizontal beam (top side) 507, and thus, crane 502, using a customized attachment, as described above. The use of a customized attachment allows for movement of the source, such as tilt and rotation in all directions. Applicant is the owner of co-pending U.S. patent application Ser. No. 12/822,183, filed on Jun. 24, 2010, which is incorporated herein by reference.

In one embodiment, the source 501 is an X-ray source, as described above. The inspection system 500 further includes an X-ray detector array 505 placed on a movable detector manipulator 506. In one embodiment, the inspection system 500 is a transmission-based system and the source 501 and detectors 505 operate via remote synchronization methods, as described earlier with reference to FIG. 2. The source 501 is movable laterally along the horizontal overhead beam 507 as shown with arrow 508. In one embodiment, the overall width 'w' of the overhead horizontal beam 507 is a function of how wide the crane 502 must be to move axially along the length of the aircraft 509 (from nose to tail) without hindrances. In other words, the width 'w' is such that the crane is 502 can easily accommodate the entire width of the aircraft, including wings, with a sufficiently comfortable margin to avoid any collisions or scraping with the aircraft body during inspection. This also ensures that source 501 can move laterally along horizontal beam 507 of crane 502 when positioned over the aircraft head wings such that the source effectively covers the aircraft wings for scanning Similarly, when the crane 502 is positioned over the tail wings, the source 501 moves laterally along the beam 507 such that it covers the tail wings for scanning.

Figure 9:
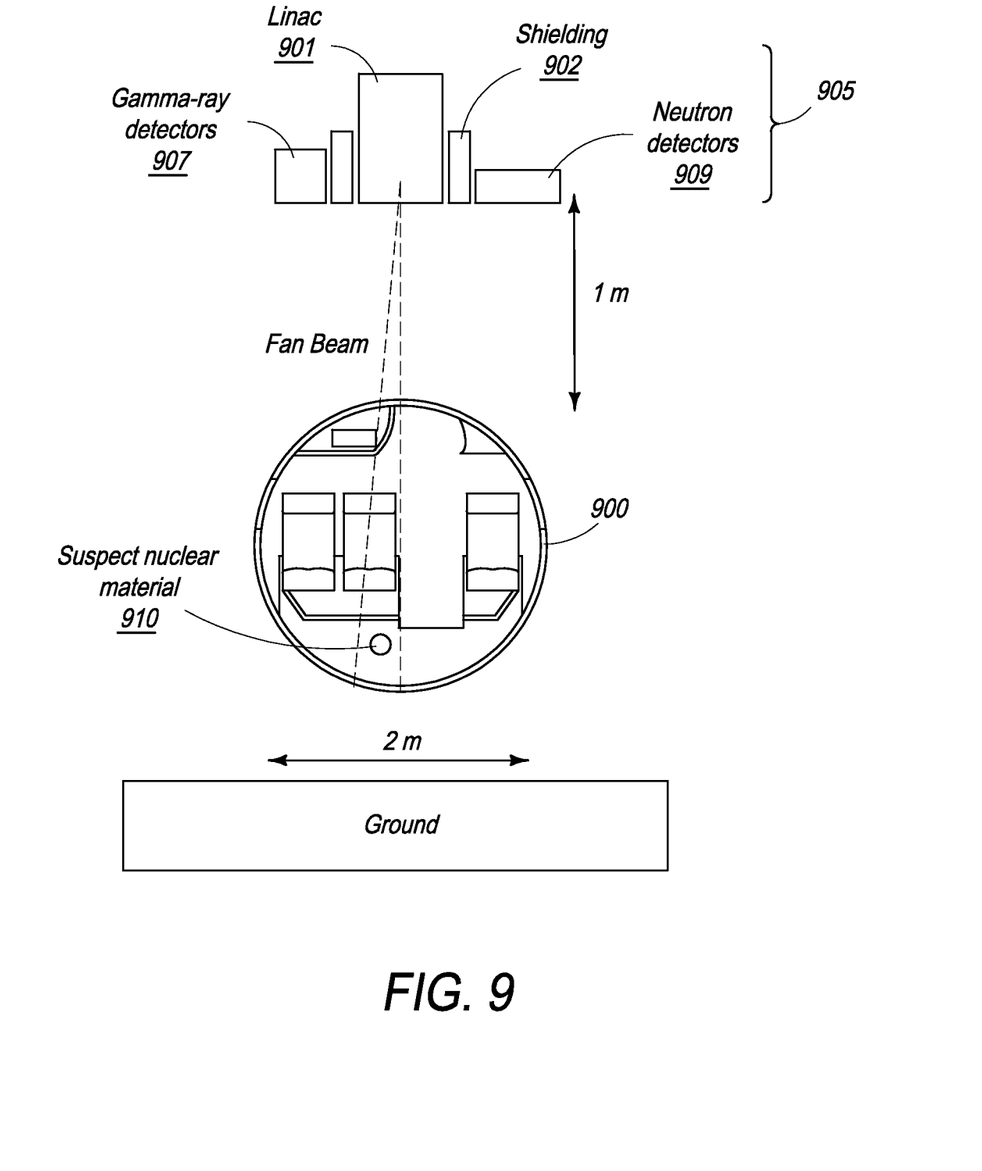
FIG. 9 is an illustration of one embodiment of a nuclear inspection configuration, including exemplary distances between an aircraft under inspection and a source/detector array.

FIG. 9, described in greater detail below, illustrates exemplary scanning distances. In one embodiment, if the aircraft under inspection 900 has a body diameter, not including wings, on the order of 2 meters, the source/detector array 905 is positioned at a distance of 1 meter from the aircraft under inspection 900, thereby achieving a sufficiently large field of view with the requisite resolution to enable radiographic inspection.

Also, in alternate embodiments, a second set of detectors are mounted on the horizontal beam 507, along with the source, to detect radiation backscattered from the aircraft. In one embodiment, the source 501 is a backscatter source module with backscatter detectors such as module 400 of FIG. 4. In this case, the backscatter head will be in closer proximity to the aircraft.

Figure 6A:
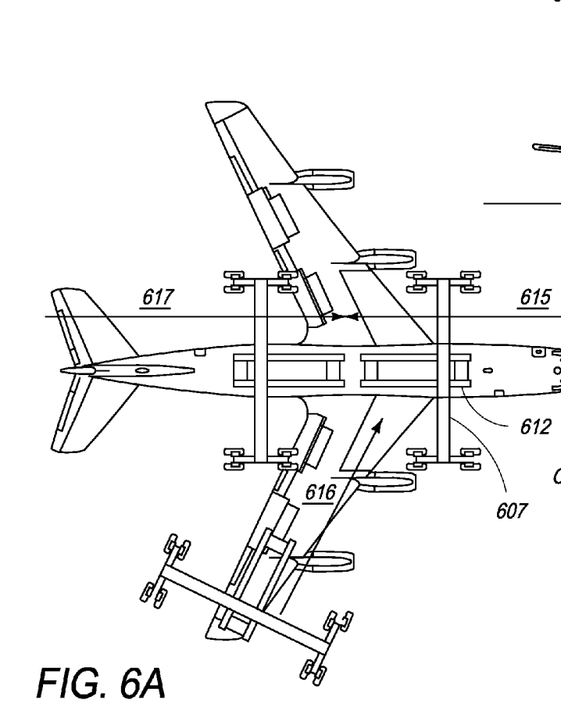
FIG. 6A is a top plan view of a multiple scan transmission-based aircraft inspection system where the source is mounted on a movable crane in accordance with yet another embodiment of the present invention.
Figure 6B:
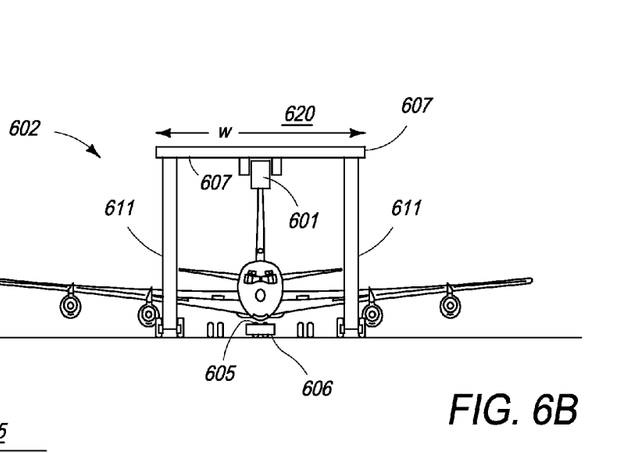
FIG. 6B is a front elevation view of the transmission-based aircraft inspection system, also shown in FIG. 6A, where the source is mounted on a movable crane in accordance with the yet another embodiment of the present invention.
Figure 6C:
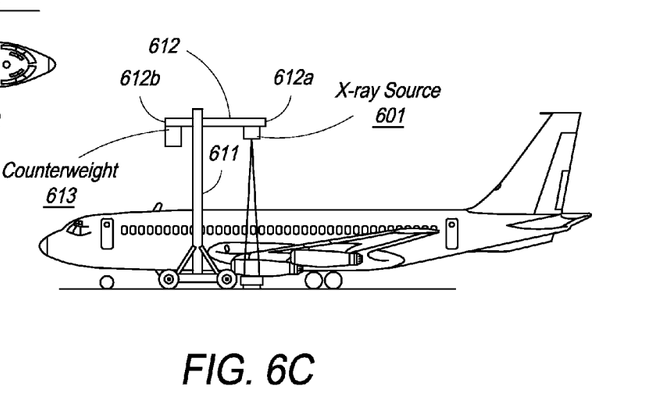
FIG. 6C is a side elevation view of the transmission-based aircraft inspection system, shown in FIGS. 6A and 6B, where the source is mounted on a movable crane in accordance with the yet another embodiment of the present invention.

FIGS. 6A through 6C show a multiple scan transmission-based aircraft inspection system where the source 601 is mounted on a movable crane 602 in accordance with yet another embodiment of the present invention. Although at least four separate scan angles are preferred in this embodiment (one for the head/nose end, one for each wing, and one for the tail end), it is advantageous in that it is capable of scanning larger aircraft compared to the inspection system described with respect to FIG. 5. Referring now to FIGS. 6A through 6C simultaneously, in one embodiment, the source 601 is an X-ray source, as described above. The inspection system further includes an X-ray detector array 605 placed on a movable detector manipulator 606. In one embodiment, the inspection system is a transmission-based system whereby the source 601 and detector array 605 on detector manipulator 606 operate via remote synchronization methods, as described earlier with reference to FIG. 2.

Referring to FIGS. 6A through 6C simultaneously, the movable crane 602 comprises two substantially parallel vertical beams 611, which form the two sides of crane 602, connected by a horizontal beam 607, which forms the top side of crane 602 thus forming a three-sided inspection gantry 620.

The width 'w' of the horizontal beam 607 is sufficient enough to enable the crane 602 to move along the length of an aircraft but not sufficient enough to allow the crane 602 to pass over the head wings of the aircraft. In one embodiment, the width 'w' is such that it can accommodate the tail wings without scraping.

In one embodiment, the horizontal overhead beam (or the top side of the gantry) 607 further supports a transverse overhanging beam 612, having a first end 612a and a second end 612b, wherein the X-ray 601 source is connected to the first end 612a of the transverse beam and a counterweight 613 is connected to the second end 612b of the transverse beam to balance the X-ray source 601. In one embodiment, first end 612a of the transverse beam 612, housing the source 601, is longer than the second end 612b, housing the counterweight 613. The transverse beam 612 is movable transversely along the width 'w' of the horizontal beam 607. For scanning operation, the crane 602 is made to pass over the aircraft once from the head-end to the wing, as shown by arrow 615, then once each for the two wings from the wing tip to the body, as shown by arrow 616, and finally once from the tail-end to the wings, as shown by arrow 617. In this manner, all the sections of the aircraft are scanned. Also, in alternate embodiments, the source 601 is a backscatter source module with backscatter detectors such as module 400 of FIG. 4. The scanning of a) the portion of the airplane from the head to the point where the wings connect to the airplane body, b) the portion of the right wing from the tip of the right wing to the point where the right wing connects to the airplane body, c) the portion of the left wing from the tip of the left wing to the point where the left wing connects to the airplane body, and d) the portion of the airplane from the tail to the point where the wings connect to the airplane body can be performed in any sequence.

The sources 501 and 601 of FIGS. 5A through 5C and FIGS. 6A through 6C, respectively, are attached to the cranes using a customized attachment, as known to persons of ordinary skill in the art, to enable tilts in all directions. The ability of the source to tilt in all directions is particularly beneficial in enabling effective scan of exclusion zones such as areas above aircraft wheels, as described in greater detail with respect to FIGS. 7 and 8.

Figure 7A:
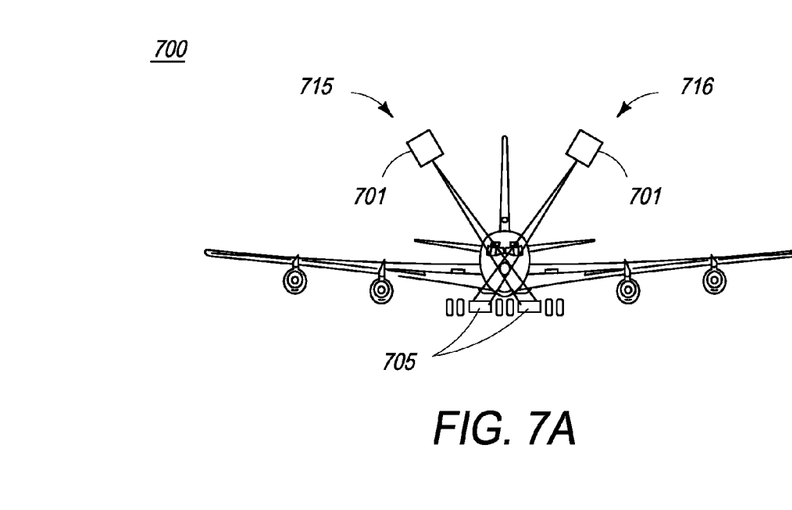
FIG. 7A is an elevation view from the nose-end or front face of the aircraft showing a first method of scanning exclusion zones such as, but not limited to, areas above the wheels.
Figure 7B:
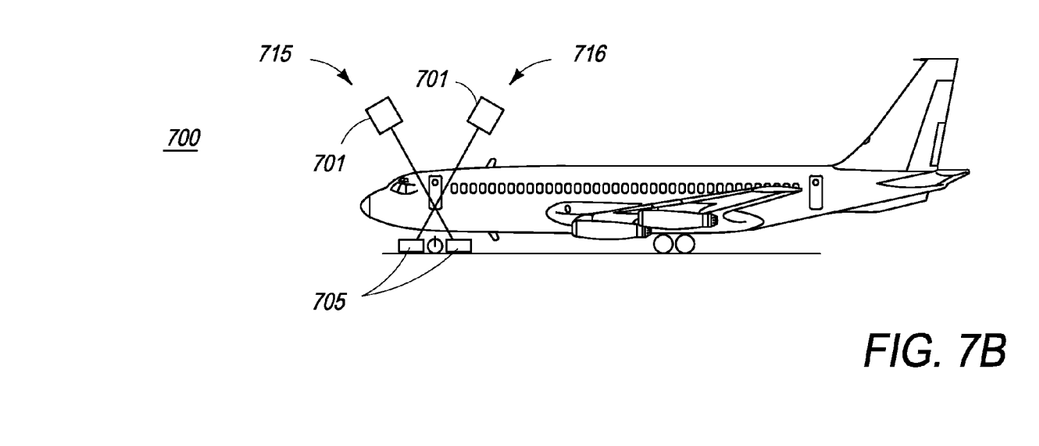
FIG. 7B is an elevation view from the side of the aircraft showing the first method of scanning exclusion zones such as, but not limited to, areas above the wheels, in a different view than FIG. 7A.

FIGS. 7A and 7B are elevation views of the aircraft showing a first method of scanning difficult to scan zones, such as, but not limited to, areas above the wheels, voids of the wings, fuselage, engine nacelles, empennage, and stabilizer areas. FIGS. 7A and 7B show tilt positions 715, 716 of source 701 when deployed using cranes 502, 602 of FIGS. 5A through 5C and FIGS. 6A through 6C, respectively to scan the areas above the wheels of the aircraft 700. The detectors 705 are placed transversely opposite to positions 715, 716. The source is moved transversely along the width of the horizontal beam of these cranes (not shown in FIGS. 7A, 7B) and then tilted to assume positions 715, 716 to scan areas above the wheels. Persons of ordinary skill in the art should note that in alternate embodiments, the source 701 could be mounted on manipulator arm of a vehicle or transport, instead of a crane, as described in system 200 of FIG. 2.

Figures 8A, 8B, 8C:
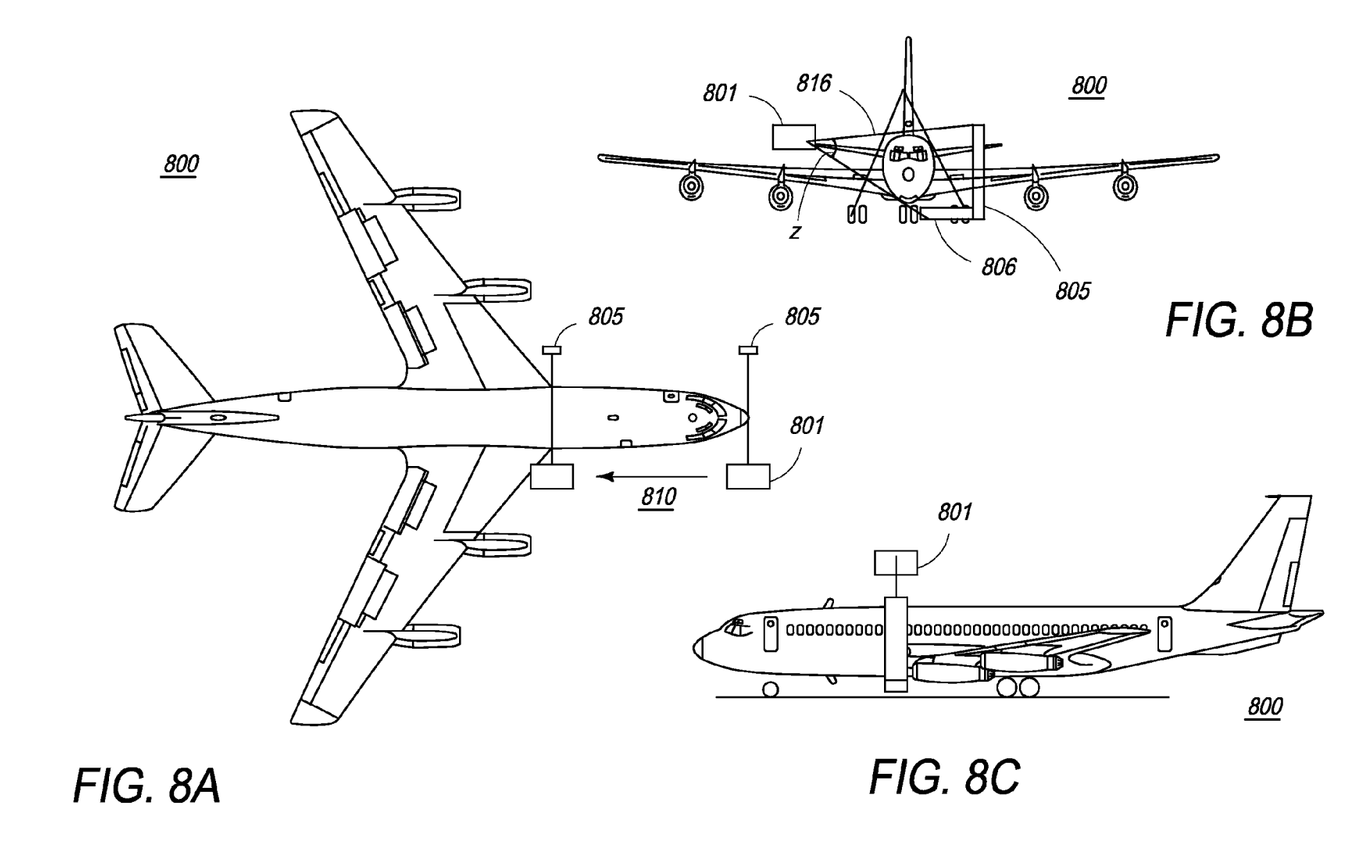
FIG. 8A is a top plan view showing a second method of scanning hidden zones such as, but not limited to, areas above the wheels.
FIG. 8B is an elevation view from the nose-end or front face of the aircraft showing the second method of scanning hidden zones such as, but not limited to, areas above the wheels, in a different view than FIG. 8A.
FIG. 8C is an elevation view from the side of the aircraft showing the second method of scanning hidden zones such as, but not limited to, areas above the wheels, in a different view than shown in FIGS. 8A and 8B.

FIGS. 8A, 8B, and 8C show alternate views of a second method of scanning difficult to scan zones on an airplane, such as, but not limited to, areas above the wheels, voids of the wings, fuselage, engine nacelles, empennage, and stabilizer areas. In this embodiment, in order to scan the areas above the wheels of the aircraft 800, the source 801 is positioned on one side of the aircraft 800 while detector arrays 805 are positioned on the opposite side. In one embodiment, the source 801 is a transmission X-ray radiation source while the detector array 805 is L-shaped to effectively capture the fan beam 816 transmitted through the aircraft. The L-shaped detectors 805 are placed on a detector manipulator 806. The source 801 and transmission detectors 805 operate via remote synchronization methods, as described earlier with reference to FIG. 2. In one embodiment, the vertical fan beam angle 'Z' and the position of the source 801 relative to the aircraft is such that the fan beam 816 is able to sweep the entire side elevation of the aircraft.

Persons of ordinary skill in the art should appreciate that the source 801 is movable by mounting on a crane or vehicle/transport as described in earlier embodiments. As shown specifically in FIG. 8A, the source 801 and detectors 805 move along the length of the aircraft as shown by arrow 810 to enable scanning of areas above the wheels.

In one embodiment, the aircraft inspection system of the present invention is capable of producing high-resolution images that enable the operator to easily identify concealed threat and contraband items. In one embodiment, a database or threat library containing standard images of airplanes is employed to compare resultant scans of the aircraft under inspection with images collected from planes of the same model to determine anomalies.

In one embodiment, depending on the size of the airplane, the images of parts of the planes are collected separately. These images can then be displayed separately, or they could be "stitched" together show a combined image.

The aircraft inspection system of the present invention is capable of accurately detecting both organic materials, such as solid and liquid explosives, narcotics, ceramic weapons, as well as inorganic materials, such as metal. In one embodiment, the aircraft imaging system uses automated threat software to alert an operator to the presence of potential inorganic and organic threat items. In one embodiment, the system is capable of transmitting backscatter and photographic images to an operator or remote inspector wirelessly.

FIG. 9 is an illustration of one embodiment of a nuclear inspection configuration, including exemplary distances between an aircraft under inspection 900 and a source/detector array 905. As described above, for an aircraft under inspection 900 having a diameter of 2 meters, the source/detector array 905 is placed at a distance of 1 meter from the aircraft 900. As shown in FIG. 9, in order to inspect for nuclear materials 910, the system includes source 901, which produces X-rays with energies of approximately 9-15 MV and/or neutrons, for example from either a d-D or d-T reaction, to induce fission to clear or confirm the presence of SNM. In the first case, gamma-ray detectors 907 are employed to measure the delayed gamma rays and neutron detectors 909 are employed to measure the delayed and/or prompt neutrons. Where neutrons are used, Differential Die-Away Analysis (DDAA) is employed to detect prompt and delayed neutrons. In both cases, high-efficiency moderated $^3$He or other neutron detectors are employed. In one embodiment, appropriate shielding 902 is employed to shield the X-ray source 901 from the gamma detectors 907 and neutron detectors 909.

The gamma-ray detectors 907 and neutron detectors 909 can also be employed for passive measurements simultaneously with the x-ray inspection. During the pulse, the X-ray system will collect data to produce images and shortly after the pulse, the passive detectors are enabled to collect gamma-rays and neutrons. The main advantage of simultaneous inspection is the reduced logistic complexity and shorter scan time compared with performing X-ray and passive detection separately. The results of the passive detection measurements and the X-ray images are data fused to improve detection of nuclear and radioactive materials.

The aircraft inspection system of the present invention is designed to be modular to enhance transportability and ease of assembly. In one embodiment, the individual modules—the vehicle, the manipulator arm, the scanning head, and optionally detector cart can be assembled on site and/or customized per application. In addition, in another embodiment, the system is ready to deploy and requires no assembly.

The system is also designed to be rugged so that it can withstand harsh environments for outdoor deployments even in inclement conditions. In one embodiment, the power required to run the system is provided on-board allowing the system to operate anywhere on the airfield. In one embodiment, the aircraft inspection system of the present invention is scalable for inspecting any aircraft size from executive jets to Airbus 380. Thus, the size of the vehicle and arm can be scaled to the size of the aircraft.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

I claim:

1. A system for externally scanning an aircraft, having a body and an underside, to detect concealed threats, the system comprising:
   a mobile gantry defined by two vertical beams connected by a horizontal beam, wherein the horizontal beam comprises a top side of said gantry, and wherein said gantry is capable of being moved along the length of the aircraft being scanned;
   an X-ray source connected to the top side of said gantry, said source capable of being moved horizontally along the top side; and
   a movable detector unit comprising a first set of detectors, said detector unit being aligned with said X-ray source and being positioned along the underside of the aircraft, such that the first set of detectors receive X-rays transmitted through the aircraft from said X-ray source.

2. The system of claim 1, wherein the positions of said X-ray source and said first set of detectors are synchronized remotely.

3. The system of claim 1, wherein the scanning motion comprises moving the mobile gantry along the length of the aircraft and moving the X-ray source along the width of the aircraft.

4. The system of claim 1 further comprising a second set of detectors disposed on the top side of said gantry for receiving the X-rays scattered back from the aircraft.

5. The system of claim 1, wherein said X-ray source is capable of being tilted in at least four directions.

6. The system of claim 1, wherein the detected threats include organic materials, inorganic materials and nuclear materials.

7. A system for externally scanning an aircraft, having a body and an underside, to detect concealed threats, the system comprising:
   a mobile gantry defined by two vertical beams connected by a horizontal beam, wherein the horizontal beam comprises a top side of said gantry, and wherein said gantry is adapted to move over at least one section of the aircraft being scanned;
   a transverse beam, having a first end and a second end, coupled to the top side of said gantry, adapted to be moved horizontally along the said top side, wherein an X-ray source is connected to the first end of said transverse beam and a counterweight is connected to the second end of said transverse beam to balance said X-ray source; and
   a movable detector unit comprising a first set of detectors, said detector unit being aligned to the X-ray source, such that the first set of detectors receive X-rays transmitted through the aircraft from said X-ray source.

8. The system of claim 7 further comprising a second set of detectors disposed along with the X-ray source for receiving the X-rays scattered back from the aircraft.

9. The system of claim 7, wherein said X-ray source is capable of being tilted in four directions.

10. The system of claim 7, wherein positions of said X-ray source and said first set of detectors are synchronized remotely.

11. The system of claim 7, wherein the detected threats include organic materials, inorganic materials and nuclear materials.

* * * * *